United States Patent [19]

Boyle

[11] 4,143,148
[45] Mar. 6, 1979

[54] ANTI-ULCER THIAZOLINE DERIVATIVES
[75] Inventor: John T. A. Boyle, Maidenhead, England
[73] Assignee: John Wyeth & Brother Limited, Maidenhead, England
[21] Appl. No.: 814,365
[22] Filed: Jul. 11, 1977
[30] Foreign Application Priority Data
Jul. 15, 1976 [GB] United Kingdom ............... 29420/76
[51] Int. Cl.$^2$ ............................................ A61K 31/425
[52] U.S. Cl. ............................... 424/270; 260/306.7 T
[58] Field of Search .................. 424/270; 260/306.7 T
[56] References Cited
U.S. PATENT DOCUMENTS
3,652,577  3/1972  Manning ....................... 260/306.7 T
OTHER PUBLICATIONS
Shadbolt, "J. Chem. Soc. ©", 1971, pp. 1667–1669.

Primary Examiner—V. D. Turner
Attorney, Agent, or Firm—Arthur E. Wilfond

[57] ABSTRACT

4-Aryl-4-hydroxythiazolines can be obtained by treatment of aroylmethyl bromides with thiourea or a N-(lower alkyl)thiourea. The hydroxythiazolines are believed to have the formula

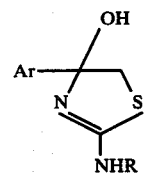

where Ar is aryl and R is hydrogen or lower alkyl. The compounds are also capable of existing in open chain tautomeric form. The compounds show anti-ulcer activity in mammals.

2 Claims, No Drawings

ANTI-ULCER THIAZOLINE DERIVATIVES

The invention relates to pharmaceutical compositions containing thiazoline derivatives, a method of using thiazoline derivatives to treat ulcers and also new thiazoline derivatives.

The Journal of The Chemical Society (Volume C), 1971, pages 1667–9, discloses the treatment of phenacyl bromide with thiourea or N-methylthiourea in acetone to give the corresponding 2-phenacylisothiouronium bromides. These compounds were assigned the tautomeric structures A, B and C

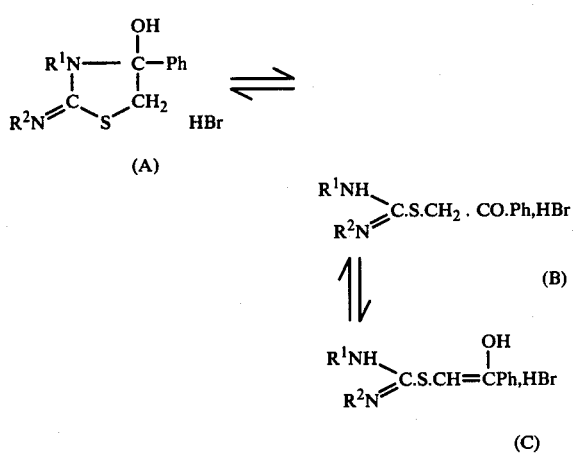

where $R^1$ is hydrogen or methyl and $R^2$ is hydrogen. The reference assigns no useful property to the compounds save that 2-phenacylisothiouronium bromide ($R^1=R^2=H$) can be dehydrated to form 2-amino-4-phenylthiazole.

The present invention is based on the finding that hydroxythiazolines obtainable by the treatment of a compound having the formula $Ar-COCH_2Br$ (wherein Ar is aryl) with thiourea or N-(lower alkyl)-thiourea of formula $RNH-CS-NH_2$ (where R is hydrogen or lower alkyl), or a tautomer thereof, in the form of the free base or a pharmaceutically acceptable acid addition salt, possess pharmacological utility. In particular the compounds possess activity as anti-ulcer agents when tested in mammals. Accordingly the present invention provides a pharmaceutical composition useful for treatment of ulcers, comprising (a) an effective amount of a compound selected from hydroxythiazolines obtainable by the treatment of an aroylmethyl bromide having the formula $Ar-CO-CH_2Br$ (where Ar is aryl, preferably phenyl or phenyl substituted by one or two substituents selected from trifluoromethyl, lower alkyl, lower alkoxy, nitro, di(lower alkyl)amino and halogen) with thiourea or a N-(lower alkyl)thiourea having the formula $RNH-CS-NH_2$ (where R is hydrogen or lower alkyl) and the tautomers of said hydroxythiazolines the compound being in a form selected from the free base and the pharmaceutically acceptable acid addition salts thereof, and (b) a pharmacologically acceptable carrier.

The invention also provides a method of treating ulcers in an afflicted mammalian host, which comprises treating the mammal with an effective amount of a compound selected from hydroxythiazolines obtainable by the treatment of an aroylmethyl bromide having the formula $Ar-CO-CH_2.Br$ (where Ar is as defined above) with thiourea or a N-(lower alkyl)thiourea having the formula $RNH-CS-NH_2$ (where R is hydrogen or lower alkyl) and the tautomers of said hydroxythiazolines, the compound being in a form selected from the free base and the pharmaceutically acceptable acid addition salts thereof.

The invention also provides, as new compounds, hydroxythiazolines obtainable by the treatment of a substituted phenacyl bromide having the formula $Ar-CO-CH_2Br$ (where Ar is phenyl substituted by one or two substituents selected from trifluoromethyl, lower alkyl, lower alkoxy, nitro, di(lower alkyl)amino and halogen) with thiourea or a N-(lower alkyl)thiourea having the formula $RNH-CS-NH_2$ (where R is hydrogen or lower alkyl) and the tuatomers of said hydroxythiazolines, the compound being in a form selected from the free base and the pharmaceutically acceptable acid addition salts thereof.

In formula A above $R^1$ is assigned as substituent of the ring nitrogen atom of the hydroxythiazoline. In fact we believe that $R^1$ substitutes the other nitrogen atom. This view is supported by the observation that the hydroxythiazoline obtained from phenacyl bromide and N-methylthiourea can be dehydrated to form 2-methylamino-4-phenylthiazole. In addition spectrographic evidence on solutions of the hydroxythiazoline obtained from phenacyl bromide and N-methylthiourea suggests that the predominant structure in solution in polar solvents is

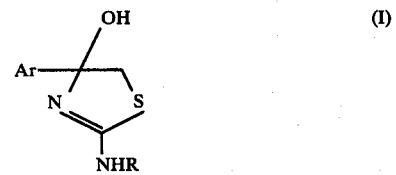

Accordingly we believe that the anti-ulcer agents provided by this invention may be assigned the structure

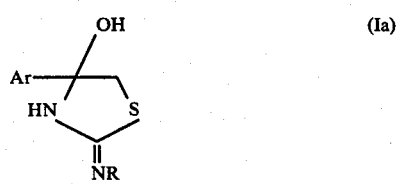

(wherein Ar is aryl and R is hydrogen or lower alkyl) and their pharmaceutically acceptable acid addition salts.

Although the compounds are illustrated as formula I above, it will be appreciated that the compounds may also exist in other tautomeric forms. In particular one possible tautomeric structure is

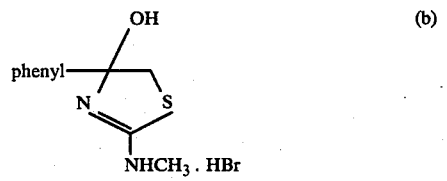

where Ar and R are as defined above. The compounds are also capable of existing in open chain tautomeric form. The open chain keto tautomeric form may be illustrated as

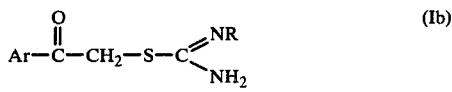

(where Ar and R are as defined above) and the corresponding enol form may be illustrated as

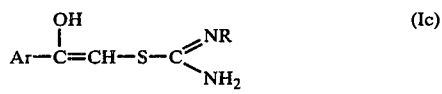

(where Ar and R are as defined above).

Different tautomeric forms may exist in equilibrium one with another and the predominant tautomer is believed to depend on such factors as whether or not the compound is solid or is in solution, or the polarity or pH of the environment. On the basis of spectrographic evidence, we believe that the predominant tautomer has the form illustrated as formula I when the compound is in solution in polar solvents as the hydrobromide. For the sake of simplicity the compounds are generally described herein on the basis of formula I, but the tautomeric forms are intended to be included as anti-ulcer agents contemplated by the invention. It is also recognised that compounds of formula I may exist as geometric isomers. These isomers are also included within the anti-ulcer agents contemplated by this invention.

Ar represents an aryl group. Examples include unsubstituted phenyl and phenyl substituted by one or more substituents conventionally used in medicinal chemistry, for example, trifluoromethyl; lower alkyl, for instance, methyl, ethyl, i-propyl, n-propyl or n-butyl; lower alkoxy, for instance, methoxy, ethoxy, i-propoxy, n-propoxy or n-butoxy; nitro; and di-(lower alkyl) amino, for instance, dimethylamino or diethylamino; or halogen, for instance, chlorine or bromine. R represents hydrogen or lower alkyl, for instance, methyl, ethyl, i-propyl, n-propyl or n-butyl. Ar is preferably unsubstituted phenyl. R is preferably hydrogen or methyl. The term "lower" as used herein with respect to alkyl or alkoxy means that the alkyl or alkoxy group contains 1 to 6 carbon atoms, preferably 1 to 4 carbon atoms. The compounds used as anti-ulcer agent in the pharmaceutical compositions of the invention are preferably in the form of a hydrohalide, advantageously hydrobromide, acid addition salt.

The anti-ulcer agents contemplates by this invention are transformed by dehydration into the corresponding 2-[amino or (lower alkyl)amino]-4-aryl thiazoles by heating in certain solvents such as ethanol. To avoid undesired dehydration it is recommended to store the hydroxythiazolines at room temperature as a solid.

The pharmaceutical compositions of this invention preferably comprise the active compound in solid form in association with a solid pharmacologically acceptable carrier material. Solid form compositions include powders, tablets and capsules. A solid carrier can be one or more substances which may also act as flavouring agents, lubricants, solubilizers, suspending agents, binders or tablet disintegrating agents; it can also be an encapsulating material. In powders the carrier is a finely divided solid which is in admixture with the finely divided active ingredients. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium tearate, talc, sugar, lactose, pectin, dextrin, starch, gelatin, tragacanth, methyl cellulose, sodium carboxymethyl cellulose, a low melting wax and cocoa butter.

Preferably the pharmaceutical composition is in unit dosage form. In such form, the composition is subdivided in unit doses containing appropriate quantities of the active ingredient; the unit dosage form can be a packaged composition, the package containing specific quantities of compositions, for example, packeted powders. The unit dosage form can be a capsule, cachet or tablet itself, or it may be the appropriate number of these in packaged form. The quantity of active compound in a unit dose of the composition may be varied or adjusted from 5 mg. to 500 mg. according to the particular need and the activity of the active compound.

The compositions of the invention will be administered orally, generally in solid composition form. The pharmaceutical compositions may also include an antacid agent. An example of a pharmaceutical composition is as follows:

EXAMPLE 1

Tablets are prepared in standard manner from a formulation consisting of, on a weight basis,

| | |
|---|---|
| 2-amino-4-hydroxy-4-phenyl-$\Delta^2$-thiazoline hydrobromide | 40% |
| Lactose B.P. 72 mesh | 18.75% |
| Avicel pH 101(1) | 40% |
| Amberlite IRP 88(2) | 2% |
| Magnesium Stearate B.P. | 0.25% |
| | 100,00% |

(1)This is a microcrystalline cellulose.
(2)This is the potassium salt of a weak acid cation exchange resin which acts as a disintegrant.

The anti-ulcer agents contemplated by this invention may be tested or evaluated by one or both of the following procedures:

Procedure A

GASTRIC SECRETION: PYLORUS-LIGATED RAT

Reference: Shay, H; Sun, D. & Gruenstein, M. Gastroenterology 26: 9060913 (1954)

Test Animal: Rat

Procedure:

Male Charles River rats, weighing 180–220 g. are deprived of food overnight, but allowed water. They are housed in separate cages with wide mesh grids, to avoid coprophagy. Next morning each rat is anesthetised with halothane, a small mid-line incision is made and the pylorus is ligated. The test compound or vehicle is administered by an appropriate route, usually by injecting a volume of 5 ml/kg into the stomach, or 1 ml/kg into the duodenum. The wound is sutured, and the animal allowed to recover. The operation takes 3–5 minutes. Four hours after pylorus ligation each rat is killed, its stomach is removed and the volume of the gastric contents is measured; the sample is discarded if it contains food or faeces.

Gastric juice is titrated against N NaOH, using a Metrohm automatic titrator. The following variables are evaluated.

1. Concentration of acid in milliequivalents per milliliter.
2. Amount of "free acid," by titrating to pH3. This result is expressed in milliequivalents of hydrogen ions per milliliter.
3. "Total acid," by further titration to pH10.
   This result is expressed as milliquivalents of hydrogen ions per milliliter.

The mean volume of gastric contents, and the three variables above, are expressed as percentage of the corresponding control values.

2-Amino-4-hydroxy-4-phenyl-$\Delta^2$-thiazoline hydrobromide and 2-amino-4-p-bromophenyl-4-hydroxy-$\Delta^2$-thiazoline hydrobromide show good anti-secretory activity in Procedure A at 30 mg/kg. 4-Hydroxy-2-methylamino-4-phenyl-$\Delta^2$-thiazoline hydrobromide shows activity in Procedure A at 10 mg/kg. and at 30 mg/kg.

Procedure B

GASTRIC ULCERS CAUSED BY COLD-RESTRAINT STRESS

Reference: Modification of procedure of Brodie, D. A. and Hanson, H, J. Appl. Physiol. 15:291–294 (1960)
Test Animal: Rat
Object: To detect compounds which will prevent ulcer formation in the grandular portion of the rat stomach.
Procedure: Male Charles River rats weighing between 120–160 gm. are deprived of food for 18 hr. with water ad lib. The rats are divided into groups of ten and dosed by the oral route with test compound, 50 mg/kg. or a vehicle control, 0.5% carboxymethylcellulose, in a volume of 5 ml/kg. Immediately after dosing the animals are inserted into aluminum restraining tubes measuring 1⅝ inches in diameter by 8 inches and placed in the cold (4 ± 1° C.). The time in the cold is adjusted so that 90% of the control animals exhibit ulcers. At the end of the test period the animals are killed, the duodenum and esophagus ligated, and the stomach removed. The stomachs are inflated with water, opened along the lesser curvature, spread over the index finger, and the mucosa wiped off to expose the submucosa. The number of hemorrhage sites in the submucosa is counted by visual observation and recorder; however, since these numbers are so variable, only the incidence of ulcer (i.e., the number of rats with ulcers) are used for evaluation.
Compounds are reported by determining a percent inhibition which is calculated as follows:

% rats with ulcers in control — % rats with ulcers in treatment X 100% rats with ulcers in control. = inhibition When tested at a dose of 5mg/kg in Procedure B, 2-amino-4-hydroxy-4-phenyl-$\Delta^2$-thiazoline hydrobromide was active. 4-Hydroxy-2-methylamino-4-phenyl-$\Delta^2$-thiazoline hydrobromide was active in Procedure B when tested at a dose of 10mg/kg. 2-Amino-4-p-bromophenyl-active in Procedure B when tested at a dose of 100 mg/kg.

The compounds used as anti-ulcer agents according to the invention may be prepared using methods known per se. We prefer to react a compound having the formula Ar—CO—CH$_2$Br (where Ar is as defined above) with thiourea or an N-(lower alkyl) thiourea of formula RNH—CS—NH$_2$ (where R is as defined above) in solution in a ketonic solvent, preferably acetone, at room temperature and recover the 2-[amino or (lower alkyl)amino]-4-aryl-4-hydroxy-$\Delta^2$-thiazoline hydrobromide formed. The hydrobromide may be converted into the free base or other acid addition salts in known manner. The preparation of the compounds is illustrated by the following examples.

EXAMPLE 2

2-Amino-4-hydroxy-4-phenyl-$\Delta^2$-thiazoline hydrobromide

Phenacyl bromide (19.9 grams) was dissolved in acetone (100 milliliters) and thiourea (7.6 grams) was dissolved in acetone (250 milliliters) and the solutions were mixed. A solid crystallized out which was collected to give 24.5 grams of the title compound, melting point 92°–95° C. (with decomposition).

Analysis: Found: C, 39.4%; H, 4.08%; N, 10.3%. C$_9$H$_{11}$BrN$_2$OS requires C, 39.3%; H, 4.03%; N, 10.2%.

EXAMPLE 3

4-Hydroxy-2-methylamino-4-phenyl-$\Delta^2$-thiazoline hydrobromide

Phenacyl bromide (19.9 grams) was dissolved in acetone (100 milliliters) and N-methylthiourea (9.0 grams) was dissolved in acetone (250 milliliters) and the solutions were mixed. After a few minutes a solid crystallised out which was collected to give 24.3 grams of the title compound melting point 130°–132° C.

Analysis: Found: C, 41.4%, H, 4.56%; N, 10.0% C$_{10}$H$_{13}$BrN$_2$OS requires C, 41.5%; H, 4.53%; N, 9.7%.

EXAMPLE 4

2-Amino-4-(p-bromophenyl)-4-hydroxy-$\Delta^2$-thiazoline hydrobromide

A solution of 6.95 grams (0.025 mole) of p-bromophenacyl bromide in 50 milliliters of acetone was mixed with a solution of 1.9 grams (0.025 mole) of thiourea in 80 milliliters of acetone. 2-Amino-4-(p-bromophenyl)-4-hydroxy-2-thiazoline hydrobromide crystallized as a colourless solid, melting point 236°–238° C. (with decomposition). The yield was 7.7 grams (87%).

EXAMPLE 5

2-Amino-4-(3,4-dichlorophenyl)-4-hydroxy-$\Delta^2$-thiazoline hydrobromide

The title compound is prepared in a manner similar to Example 4 by using 3,4-dichlorophenacyl bromide instead of p-bromophenacyl bromide.

EXAMPLE 6

4-(p-Diethylaminophenyl)-4-hydroxy-2-methylamino-$\Delta^2$-thiazoline hydrobromide The title compound is prepared in a manner similar to Example 4 using p-diethylaminophenacyl bromide instead of p-bromophenacyl bromide and N-methylthiourea instead of thiourea.

EXAMPLE 7

2-Amino-4-hydroxy-4-(m-nitrophenyl)-$\Delta^2$-thiazoline hydrobromide

The title compound is prepared in a manner similar to Example 4 using m-nitrophenacylbromide instead of p-bromophenacyl bromide.

EXAMPLE 8

2-Amino-4-hydroxy-4-(p-trifluoromethylphenyl)-$\Delta^2$-thiazoline hydrobromide The title compound is prepared in a manner similar to Example 4 using p-trifluoromethylphenacyl bromide instead of p-bromophenacyl bromide.

EXAMPLE 9

2-Amino-4-hydroxy-4-(p-methylphenyl)-$\Delta^2$-thiazoline hydrobromide

The title compound is prepared in a manner similar to Example 4 using p-methylphenacyl bromide instead of p-bromophenacyl bromide.

EXAMPLE 10

2-Amino-4-hydroxy-4-(p-methoxyphenyl)-$\Delta^2$-thiazoline hydrobromide

The title compound, melting point 228°–229° C. is prepared in a manner similar to Example 4 by using p-methoxyphenacyl bromide instead of p-bromophenacyl bromide.

EXAMPLE 11

4-Hydroxy-4-(p-methoxyphenyl)-2-methylamino-$\Delta^2$-thiazoline hydrobromide.

The title compound, melting point 148°–150° C., is prepared in a manner similar to Example 10 using N-methylthiourea instead of thiourea.

What is claimed is:

1. A method of treating ulcers in an afflicted mammal, which comprises orally administering to said mammal a therapeutically effective amount of a compound selected from hydroxythiazolines obtainable by the treatment of an aroylmethyl bromide having the formula Ar—CO—CH$_2$Br, wherein Ar is phenyl or phenyl substituted by one or two substituents selected from the group consisting of trifluoromethyl, lower alkyl, lower alkoxy, nitro, di(lower alkyl)amino and halogen, with thiourea or a N-(lower alkyl)thiourea having the formula RNH—CS—NH$_2$, wherein R is selected from the group consisting of hydrogen and lower alkyl, and the tautomers of said hydroxythiazolines, the compound being in the form of the free base or a pharmaceutically acceptable acid addition salt thereof.

2. A method as claimed in claim 1, wherein Ar is phenyl and R is hydrogen.

* * * * *